United States Patent [19]

Coull et al.

[11] Patent Number: 5,410,068

[45] Date of Patent: Apr. 25, 1995

[54] SUCCINIMIDYL TRITYL COMPOUNDS AND A PROCESS FOR PREPARING SAME

[75] Inventors: James M. Coull, Acton; Brian Gildea, Canton; Hubert Koester, Concord, all of Mass.

[73] Assignee: PerSeptive Biosystems, Inc., Cambridge, Mass.

[21] Appl. No.: 425,740

[22] Filed: Oct. 23, 1989

[51] Int. Cl.⁶ .............................................. C07D 207/40
[52] U.S. Cl. ...................................... 548/545; 548/215; 536/25.31
[58] Field of Search ................... 260/413; 424/195.1; 514/12–19, 23, 44, 169, 44–51; 530/324, 350; 536/18.6, 27–29, 25.3, 25.31; 548/545

[56] References Cited

U.S. PATENT DOCUMENTS 4,914,210 4/1990 Levenson et al. .................. 548/413
4,968,788 11/1990 Farquhar ............................. 536/27

OTHER PUBLICATIONS

Jaunton-Rigby et al., J. Org. Chem., vol. 37, No. 7, 1972 pp. 956–964.
Sekine M. and T. Hata, *J. Am. Chem. Soc.* 106:5763–5764 (1984).
Sekine, M. and T. Hata, *Bull. Chem. Soc. Jpn.* 58:336–339 (1985).
Seliger, V. H. and H.-G. Gortz; *Angew. Chem. Int. Ed. Engl.* 20:683–684 (1981).
Schmidt, G. et al., *Nucleosides and Nucleotides* 7:795–799 (1988).
Happ, E. and C. S. Happ, *Nucleosides and Nucleotides,* 7:813–816 (1988).
Kwiatkowski, M. and J. Chattopadhyaya, *Acta. Chemi. Scan.* B38:657–671 (1984).
Gildea, B. D. et al., Abstract from the American Assoc. of Clin. Chemistry, 4th San Diego Conference on Nucleic Acid Applications, San Diego, Calif. (Oct. 25–27, 1989).

*Primary Examiner*—John W. Rollins
*Assistant Examiner*—J. Oliver Wilson
*Attorney, Agent, or Firm*—Testa, Hurwitz & Thibeault

[57] ABSTRACT

The invention pertains to compounds and methods for the reversible modification of natural products, biopolymers or synthons for natural products or biopolymers, such as nucleosides, nucleotides, and oligonucleosides. The modification enables one to perform a variety of chemistries on these compounds, yet can be removed to regenerate functional groups on the natural products, biopolymer or synthon of interest.

2 Claims, 3 Drawing Sheets

SUCCINIMIDYL TRITYL COMPOUNDS AND A PROCESS FOR PREPARING SAME

BACKGROUND OF THE INVENTION

During the chemical synthesis of multifunctional compounds, it is often necessary to use protecting groups so that selective chemical transformations can be performed. Ideally, a protecting group should allow for simple and efficient protection and subsequent regeneration of a functional group on the deprotected compound. Protecting groups which may irreversibly alter the functional group should be avoided. Moreover, the products should also be easily purified from side products generated during the synthesis or during the cleavage of the protecting group.

Triphenylchloromethane (also known as triphenylmethyl chloride and trityl chloride) and related derivatives have long been used for the protection of hydroxyl groups, amino groups and thiol groups. See Greene, T. W., *Protecting Groups in Organic Synthesis*, John Wiley and Sons, NY (1981). The triphenylmethyl cation is a sterically hindered electrophile. This property results in preferential reactivity of the trityl halide species with less hindered nucleophiles. In oligonucleotide synthesis, the 4,4'-dimethoxytriphenylmethyl-(4,4'-dimethoxytrityl) group and related 9-phenylxanthene-9-yl (more commonly known as pixyl) group are commonly used for the regioselective protection of the 5'-hydroxyl group of ribonucleoside and 2'-deoxyribonucleoside monomers.

Characteristics such as preferred acid lability, hydrophobic character and 5'-regioselectivity make these two triphenylmethyl derivatives the protecting groups of choice in oligonucleotide synthesis.

Alkoxy substitution of the phenyl rings is commonly used to increase the acid lability of the triphenylmethyl protecting group. Detailed investigation of trityl derivatives and the effects of substituents on acid lability have been performed. (Taunton-Rigby, A. et al., *J. Org. Chem.* 37:956-964 (1972). Appropriate substitution affords the 4,4'dimethoxytriphenymethyl group and the 9-phenyl-xanthene-9-yl group of optimal acid lability for current oligonucleotide synthesis applications. Additionally, several acid stable trityl derivatives which retain the desirable hydrophobic character and 5'-regioselectivity have been prepared, such as 4,4', 4"-tris(4,5-dichlorophthalimido)-trityl (Sekine, M. and T. Hata, J. Am. Chem. Soc. 106:5764-5765 (1984)); 4,4',4"-tris(-levulinyloxy)trityl (Sekine, M. and T. Hata, *Bull. Chem. Soc. Jpn.*, 58:336-339 (1985)); 4-(9-fluorenylmethyloxycarbonyl)oxy-4'4"-dimethoxytrityl (Happ, E. and C. S. Happ, *Nucleosides and Nucleotides* 7:813-816 (1988)); and 4-(9-fluorenylmethyloxycarbonyl)amino-4',4"-dimethoxytrityl (ibid.). All these compounds are substituted triphenylmethyl derivatives containing protected phenol(s) or protected exocyclic amino group(s). While the phenol(s) or exocyclic amino group(s) remain protected, the trityl ether bond is fairly stable to acidic conditions. Upon hydrazinolysis of the levulinyl protecting groups, hydrazinolysis of the 4,5-dichlorophthalimido protecting groups or alkali catalyzed beta-elimination of the 9-fluorenylmethyloxycarbonyl (Fmoc) group, the phenolic group(s) or exocyclic amino group(s) were all regenerated. The ether bond of the resulting trityl species can then be rapidly cleaved with mild acid. Trityl derivatives which have been previously described served strictly as protecting groups having unusual lability characteristics.

Triphenylmethyl protecting groups with long chain alkyl substituents have been prepared as tools for affinity chromatographic purification of oligonucleotides. Seliger, H. and H. H. Gortz, *Angew. Chem.* 93:709 (1981); Seliger, H. and H. H. Gortz, *Angew. Chem. Inter. Ed. Engl.* 20:683 (1981); Kwiatkowski, M. et al., *Acta. Chem. Scand.* B38:657 (1984); Schmidt, G. et al., *Nucleosides and Nucleotides* 7:795-799 (1988). By introducing triphenylmethyl protecting groups bearing long chain alkyl substituents to the 5'-hydroxyl terminus of oligodeoxynucleotides, stronger affinity of the full length DNA products for hydrophobic chromatographic supports can be achieved. Such derivatives are particularly useful for the purification of oligonucleotides of greater than sixty nucleotides in length. However, preparation of the long chain alkyl substituted triphenylmethyl derivatives and the four suitably protected synthetic monomers is difficult and labor intensive. These monomers are used for a single condensation reaction in an oligonucleotide synthesis.

In recent years, non-isotopic labeling of oligodeoxynucleotides utilizing biotin and fluorophores has become increasingly useful for the detection of DNA immobilized on solid supports (Beck, S. et al., *Nucl. Acids Res.* 17:5115-5123 (1989)); Takahashi, T. et al., *Anal. Biochem.* 179:77-85 (1989); the immobilization of DNA to solid supports (Syvanen, A. et al., *Nucl. Acids Res.* 16:11327-11338 (1988)); Richardson R. W. and Gumport, R. I., *Nucl. Acids Res.* 11:6167-6184 (1983)); the affinity purification of DNA (Mitchell, L. G. and Merril, C. R., *Anal. Biochem.* 178, 239-242 (1989)); Dawson, B. A. et al., *J. Biol. Chem.* 264, 12830-12837 (1989)); and/or the sequencing of DNA (Beck, Ibid; Mitchell, et al., Ibid.; Smith, L. M., *Nature* 321:674-679 (1986)). Biotin and fluorophores have been incorporated into synthetic nucleic acid fragments by numerous chemical methods (Agrawal, S. et al., *Nucl. Acids Res.* 14:6227-6245 (1986); Forster, A. C. et al., *Nucl. Acids Res.* 13:745-761 (1985); Coull, J. M. et al., *Tett. Lett.* 27:3991-3994 (1986); Gibson, K. J. and Benkovic, S. J., *Nucl. Acids Res.* 15:6455-6467 (1987).

Chemical assembly of oligonucleotides is well established and has been performed by phosphodiester, phosphotriester, phosphoramidate, phosphoramidite and H-phosphonate methods. See Gait, M. J., *Oligonucleotide Synthesis, A Practical Approach*, IRL Press Inc., Oxford, England. The most common means by which oligonucleotides are produced is referred to as solid phase synthesis using the 2-cyanoethylphosphoramidites (Sinha, N. D. et al., *Nucleic Acids Research*, 12:4539-4557 (1984); and U.S. Pat. No. 4,725,677, issued to Millipore Corporation). Several suitably protected amino groups containing nucleoside derivatives (Haralambidis, J., et al., *Nucl. Acids Res.* 15:4857-4876 (1987); Gibson, K. J., Ibid., Smith, L. M. et al., *Nucl. Acids. Res.* 13:2399-2412 (1985)), thiol group containing nucleoside derivatives (Sproat, B. S., et al., *Nucl. Acids Res.* 15:4837-4848 (1987)) and 5'-terminal linkers (Agrawal, S., Ibid.; Coull, J. M. et al., Ibid.; Connolly, B. A., *Nucl. Acids Res.* 15:3131-3139 (1987); Blanks, R. and McLaughlin, L. M., *Nucl. Acids Res.* 16:2659-2669 (1988); Connolly, B. A. and Ridge, P., *Nucl. Acids Res.* 13:4485-4502 (1985)) have been prepared for DNA labeling applications. All of these synthons are easily incorporated into oligodeoxynucleotides during chemical assembly. All of these linkers can be further reacted to introduce a label into the oligonucleotide. The linkers, however, cannot be removed to generate a natural (unmodified) oligonucleotide.

The polymerase chain reaction (PCR) (U.S. Pat. No. 4,683,202 issued to Cetus Corporation) is a method used to exponentially amplify a nucleic acid sequence in vitro. The method uses two short oligonucleotide primers which are complementary to different strands of a DNA template and flank the region of the nucleic acid sequence to be amplified. Using a thermostable DNA polymerase and repeated cycles of template denaturing, primer annealing and primer extension, it is possible to rapidly prepare large quantities of a defined nucleic acid sequence from a few or even a single template copy. However, the flanking sequences must first be determined in order to prepare complementary primers.

Primers used in PCR will be incorporated at the 5'-hydroxyl terminus of the amplified products. If one (or both) of the primers are labeled in such a manner as not to interfere with primer annealing and primer extension, it is inevitable that the amplified product will contain the label. It would be desirable to chemically assemble oligonucleotide primers in which the label can be later removed to yield unmodified DNA.

The immobilization of PCR amplified products to a solid support has been performed by using biotin-labeled primers and a streptavidin agarose support (Mitchell, L. G., et al., *Anal. Biochem.* 178:239-242 (1989)). When a single labeled primer is used, it was possible to denature the immobilized double-stranded product and isolate the single-stranded sequence extended from the unlabeled primer. However, the affinity of the biotin-streptavidin complex is so great ($K_d$ is reported to be $10^{-15}$) that it is essentially impossible to remove the biotin-labeled strand from the support, thus interfering with isolation of the double-stranded product. Moreover, based on the limitations afforded by current oligonucleotide synthesis and labeling chemistries, it would be desirable to have a method in which biotin can be cleaved from the amplified DNA so that the unmodified double-stranded product can be obtained.

SUMMARY OF THE INVENTION

This invention pertains to heterobi- or oligo-functional protecting groups in which at least two functionalities can regioselectively or chemoselectively bind to functional groups on a natural product, biopolymer or synthon for a natural product or biopolymer (such as, an oligonucleotide, nucleic acid, nucleoside, nucleotide, amino acid, monosaccharides, oligosaccharides, peptides, proteins, carbohydrates, lipids, steroids or alkaloids). The protecting groups provide a means to reversibly attach a modifying group to the natural product, biopolymer or synthon. The biopolymer, natural product or synthon can be regenerated in original form by simply removing the protecting group. In general, the protecting group comprises a regioselective or chemoselective functionality and one or more additional functionalities which can bind to a modifying moiety, such as a detectable label, a biologically active molecule or a compound for aiding in the purification of the natural product, biopolymer or synthon. Preferably, the protecting group is a triphenylmethyl derivative, such as 4,4'-dimethoxytriphenylmethyl or pixyl.

The invention also pertains to reversibly modified natural product, biopolymer and synthon which can be represented by the formula:

L—P—C* wherein C* is a natural product, biopolymer or synthon for a biopolymer or natural product; P is a protecting group bound to a functional group of C* which can be removed from the protected functional group under conditions such that the functional group is regenerated; and L is a functionality for bonding a modifying moiety to P.

The heterobi- or oligofunctional protecting groups of this invention can be used as a vehicle for reversibly attaching a natural product, biopolymer or synthon to the modifying moiety. Although one or more functionalities on C* are protected by P, one can perform a variety of chemical manipulations. For example, single-stranded and double-stranded nucleic acids can be purified and subsequently isolated in their natural form. Likewise, several natural products can be simultaneously purified and separated from each other using the methods and compounds described herein. In one embodiment, modified oligonucleotides can be used as primers for polymerase chain reactions.

DETAILED DESCRIPTION OF THE INVENTION

This invention pertains to compounds which serve as both a protecting group for protection of a functional group on a natural product, biopolymer or synthon for a natural product or biopolymer; and a linking group for attaching a modifying moiety thereto. The compounds of this invention are heterobi- or oligofunctional protecting groups in which at least one functionality can regioselectively or chemoselectively bind to a functional group of the natural product, biopolymer or synthon. They, however, can be removed from the protected functional group under conditions such that the original functional group is regenerated.

Heterobi- or oligofunctional protecting groups can be represented by the formula L—P, where P is a protecting group for protection of a functional group on the natural product, biopolymer or synthon. For example, P can be used to protect hydroxyl, amino or thiol functionalities. The protecting group is capable of being removed from the protected functional group under conditions such that the original functional group is regenerated. Preferably, P is a regioselective protecting group, such as trityl, 4-monomethoxytrityl, 4,4'-dimethoxytrityl or pixyl. However, other protecting groups can be used depending upon the functionality on the natural product, biopolymer or synthon to be protected. P can also be benzyl (e.g., methoxybenzyl, nitrobenzyl, alkoxybenzyl, dialkoxybenzyl); benzyloxycarbonyl (e.g., methoxylbenzyloxycarbonyl); benzyloxymethyl (e.g., nitrobenzyloxymethyl, methoxybenzyloxymethyl); alkoxycarbonyl (e.g., t-butoxycarbonyl); alkoxymethyl (e.g., methoxymethyl); alkylsilyl (e.g., t-butyldimethylsilyl); arylsilyl (e.g., triphenylsilyl); benzoyl (e.g., nitrobenzoyl, alkoxybenzoyl); phenoxyacetyl; or alkoxyacetyl. Each of these protecting groups can be substituted. For example, a preferred protecting group for peptide synthesis is 9-fluorenylmethyloxycarbonyl.

L is a functionality on the protecting group for bonding or linking a modifying moiety thereto. Reaction, extension, additional functional group incorporation or labeling can be performed at this site since L is a reactive group.

This invention also pertains to reversibly modified natural products, biopolymers or synthons which can be represented by the formula: L—P—C* where C* represents a synthetic biopolymer, synthon, natural product or any modification of these. C* can be a nucleoside, nucleotide, oligonucleotide, nucleic acid, amino acid peptide, protein, monosaccharide, oligosaccharide, carbohydrate, steroid, lipid or alkaloid. Attachment of a modifying moiety to L results in a compound represented by the formula M—L—P—C*, where M is the modifying moiety. Upon subjecting the product M—L—P—C* to conditions suitable to remove the protecting group, the original deprotected functional group of compound C* will be generated along with the biproduct M—L—P.

The modifying moiety M represents either the original modifiying moiety or any modification thereof. M can be a means for detecting and/or purifying C*, such as by affinity or non-affinity purification methods. M can also serve as a means for attaching C* to a solid support. Accordingly, M can be an alkyl moiety, a hydroxyalkyl moiety, a carboxyalkyl moiety, an aminoalkyl moiety, a thioalkyl moiety, a detection label (such as a radioisotope, fluorophore, luminescent compound, chemiluminescent compound or biotin), an affinity or purification handle (such as long alkyl chains, polymers or biological molecules), a biologically active molecule (such as a peptide, a protein, a nucleoside, a nucleotide, an oligonucleotide, a nucleic acid, a sugar molecule, an oligosaccharide, carbohydrate, steroid, lipid or alkaloid) or a polymer. For example, when the M is a detection label, it is possible to detect the complex M—L—P—C* by an appropriate means. Deprotection regenerates the compound C* and the labeled biproduct M—L—P. Removal of the protecting group may or may not be performed after the separation, isolation, detection and/or purification of the complex.

When M is a compound for aiding in the purification or immobilization of C* (such as a purification or affinity handle) it is possible to pass the complex M—L—P—C* over a solid support to selectively adsorb or covalently attach the complex to the support for the purpose of immobilization and/or purification. In the case where the complex M—L—P—C* can be eluted from the support, it is possible to collect the purified product. Removal of the protecting group under predefined conditions will generate C* and the biproduct M—L—P. When the complex M—L—P—C* is strongly immobilized to the support via the modifying moiety M, the new species will be defined as S—M—L—P—C* where S is defined as the support. C* can then be separated from the biproduct S—M—L—P under conditions known to remove the protecting group, such as by acid treatment.

One or more chemical or enzymatic manipulations of compound C* of the complex M—L—P—C*. can be performed to prepare a modified compound defined as C*. Although C* has been previously defined to include modified versions of C*, for illustration purposes C*' represents one or more modifications. The resulting complex defined as M—L—P—C*' is capable of yielding C*' and a biproduct M—L—P upon exposure of the complex to conditions sufficient to remove the protecting group. Similarly, one or more chemical or enzymatic manipulations can be made to M of complex M—L—P—C*. Such manipulations can be made prior to or after C, is chemically or enzymatically manipulated. Likewise, M—L—P can be removed from C* or C*' upon condition dependent removal of the protecting group.

A preferred protecting group is a triphenylmethyl derivative which is modified such that it can bind to C* for protection thereof and to a modifying group (such as a label) at one or more other functional groups on the phenyl moieties. Generally, heterobi- or oligofunctional triphenylmethyl protecting groups of this invention are represented by the formula:

For example, when C* is a nucleoside, nucleotide or oligonucleotide, the triphenylmethyl protecting group (P) can be bound to C* at the 5'-hydroxyl group, the nucleoside base or the 3'-hydroxyl group. Preferably, P is attached to the 5'-hydroxyl group. C* can be cleaved from the complex at the protecting group to thereby yield the original unprotected biological compound. Thus, biological compounds of interest can be removed from labels or other modifying moieties without altering their structures due to the removal procedure. Preferred triphenylmethyl derivatives and methods for making them are described in detail below.

In one embodiment, a substituted triphenylhydroxymethyl derivative containing a single (or multiple) exocyclic carboxylic acid, sulfonic acid, cyano, nitro or other functional group(s) of the general formula (Ia) is prepared. Likewise, a substituted triphenylhydroxymethyl derivative containing a single (or multiple) exocyclic alkyl carboxylic acid, alkyl sulfonic acid, cyanoalkyl, nitroalkyl or other alkyl functional group(s) of the general formula (Ia) is prepared.

Ia wherein $A_1$–$A_{15}$ are the same or different and are selected from the group consisting of H, R, OR and Z, provided that there is at least one Z group; R is an alkyl having one to 20 carbon atoms (e.g., methyl, ethyl, 2-propyl, butyl, t-butyl, 2-cyanoethyl), which is optionally substituted by one or more heteroatoms (such as a cyano, nitro or halo group; or a substituted or unsubstituted aryl (e.g., phenyl t-butylphenyl); and Z is —$(CH_2)_nC(O)OH$, —$(CH_2)_nSO_3H$, —$(CH_2)_nNO_2$, —$(CH_2)_nCN$, —$(CH_2)_nOH$, —$(CH_2)_nNH_2$ or —$(CH_2)_nSH$ where n is an integer from zero to 20; provided that when n is zero, Z is a group other than —OH or —$NH_2$.

Figure 1:
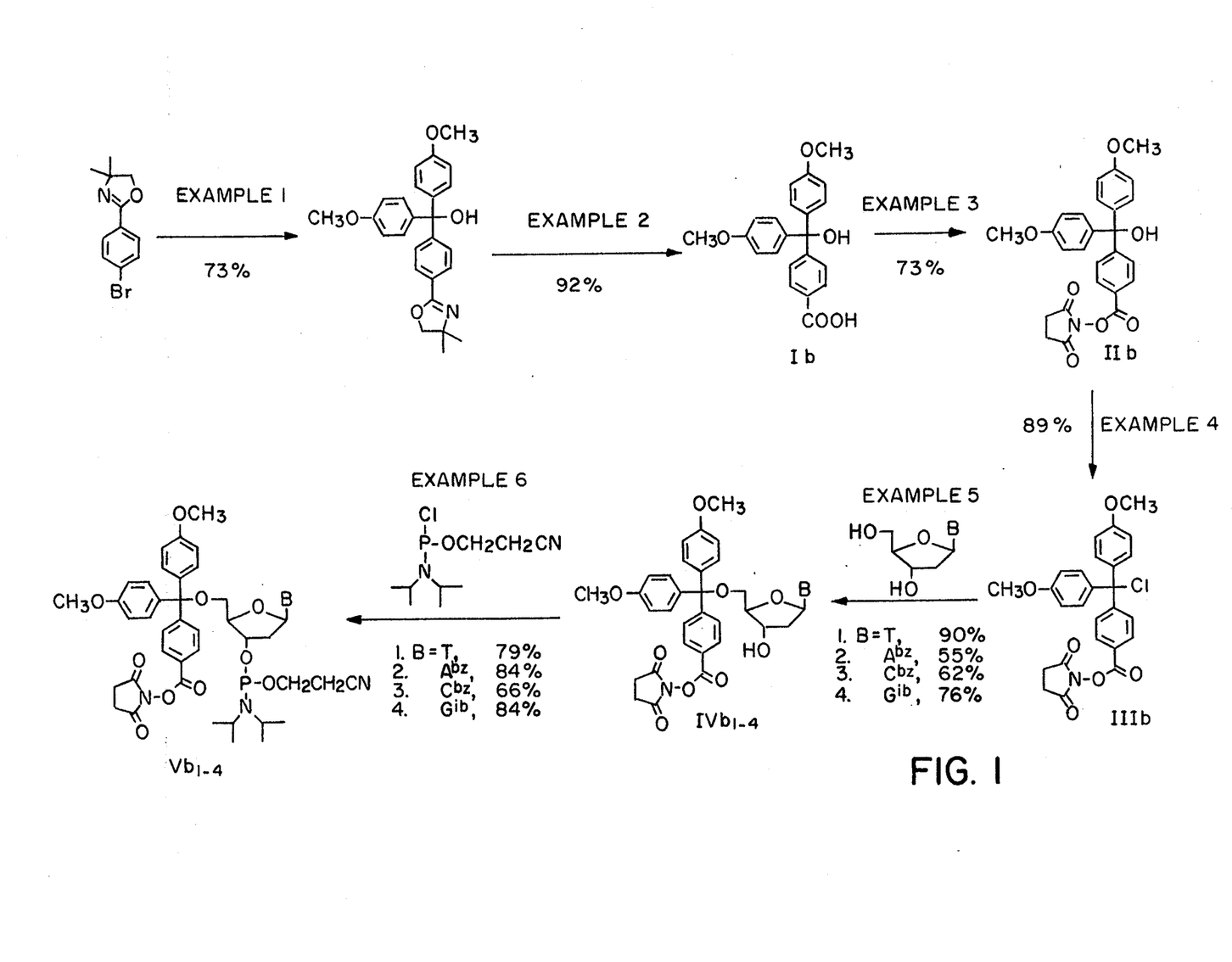
FIG. 1 is a schematic representation of the synthesis of a modified triphenylmethyl protecting group and a nucleoside protected therewith.

A preferred derivative of the above compound is a 4′,4″-dimethoxytriphenylhydroxymethyl shown in FIG. 1 (compound Ib). According to FIG. 1, the compound can be synthesized by reacting a Grignard reagent (prepared from 2-(4-bromophenyl)-4,4-dimethyl-1,3-oxazoline and magnesium) with a substituted or unsubstituted benzophenone to produce a substituted or unsubstituted triphenylmethyl derivative. This compound is then sequentially treated with aqueous acid, base and acid to yield the compound Ib.

The exocyclic functional group(s) of the compounds of the general formula (Ia) is converted to a compound of general formula IIa. In one embodiment, the exocyclic functional group is converted to a compound having an exocyclic electrophilic functional group, such as N-hydroxysuccinimidyl ester, 2-nitrophenyl ester, 4-nitrophenyl ester, 2,4-dichlorophenyl ester, any active ester, an acyl halide, acyl azolide, alkyl halide, a sulfonyl halide or any reactive halide derivative. Preferably, the compound is N-succinimidyl-4-[bis(4-methoxyphenyl)-hydroxymethyl]benzoate (IIb) shown in FIG. 1.

IIa wherein $A'_1$–$A'_{15}$ are the same or different and are selected from the group consisting of H, R, OR, Z and L, provided that there is at least one L group; R and Z are defined above; L is —$(CH_2)_nC(O)W$, —$(CH_2)_nSO_2W$, —$(CH_2)_nW$, where n is an integer from zero to 20; and W is selected from the group consisting of Cl, Br, I, —NCS, —NCO, and $D_1$–$D_5$ are the same or different and from H, F, Cl, Br, I, —$NO_2$ and —CN.

A substituted triphenylhalomethyl or triphenyltetrafluoroboranomethyl derivative containing an exocyclic reactive site(s) of the general formula IIIa can then be prepared from compounds of the general formula IIa. For example, a triphenylhalomethyl or triphenyltetrafluoroboranomethyl derivative containing at least one additional exocyclic electrophilic functional group can be prepared. These compounds are regioselective dielectrophilic triphenylmethyl derivatives. Preferable exocyclic electrophilic functional groups include N-hydroxysuccinimidyl ester, 2-nitrophenyl ester, 4-nitrophenyl ester, 2,4-dichlorophenyl ester, any active ester, an acyl halide, acyl azolide, alkyl halide, a sulfonyl halide or any reactive halide derivative. In a preferred embodiment, the compound is N-succinimidyl-4-[bis(4-methoxyphenyl)chloromethyl]-benzoate (IIIb) shown in FIG. 1.

IIIa wherein $A'_1$–$A'_{15}$ are defined above and X is a leaving group, such as Cl, Br, I or $BF_4$.

Regioselective protection of a functional group on a natural product, biopolymer or synthon for a natural product or biopolymer is achieved by preferential reactivity at the sterically hindered cationic site of compounds having the general formula IIIa, to form a compound of general formula IVa. For example, the 5′-hydroxyl group of a ribonucleoside or 2′deoxyribonucleoside is preferentially protected with the triphenylmethyl derivatives of general formula IIIa, to yield partially protected nucleoside derivatives having the general formula IVa.

wherein $A'_1$–$A'_{15}$ are defined above, and C* is selected from the group consisting of a nucleoside, nucleotide, oligonucleotide, nucleic acid, amino acid, peptide, protein, monosaccharide, oligosaccharide, carbohydrate, lectin, lipid, steroid, alkaloid, and a biopolymer.

Preferred compounds of the formula IVa are N-succinimidyl-4-[bis(4-methoxyphenyl)-5'-O-(2'-deoxyribonucleosidyl)-methyl]-benzoate (IVb1-4; FIG. 1) and N-succinimidyl-4-[bis(4-methoxyphenyl)-5'-O-(ribonucleosidyl)-methyl]-benzoate. These compounds can be represented by the formula IVc.

wherein B is a nucleoside base which may be protected by a base protective group which can be eliminated (Köster, H. et al., *Tetrahedron* 37:363–369 (1981), and can be selected from the group consisting of:

Q is H or methyl;
G is H, OH, OR,

R is defined above

To prepare fully protected nucleoside derivatives, the 3'-hydroxyl group of the partially protected nucleoside derivatives of general formula IVc are reacted with an activated phosphorus containing compound. Fully protected nucleoside derivatives which result from this reaction are represented by formula Va. Compounds of this formula are suitable for subsequent condensation with a hydroxyl group under the conditions commonly used for oligonucleotide synthesis. Activated phosphorus compounds which can be used include but are not limited to 2-cyanoethylphosphoramidites (U.S. Pat. No. 4,725,677), O-methyl phosphoramidites (U.S. Pat. No. 4,458,066), H-phosphonate synthons, phosphotriester synthons, and phosphodiester synthons. Two examples of fully protected nucleoside derivatives are N-succinimidyl-4[bis(4-methoxyphenyl)-5'-O-(3'-O-(N,N-diisopropylamino-2-cyanoethylphosphinyl)-ribonucleosidyl)-methyl]-benzoates and N-succinimidyl-4-[bis(4-methoxyphenyl)-5'-O-(3'-O-(N,N-diisopropylamino-2-cyanoethylphosphinyl)-2'-deoxyribonucleosidyl)-methyl]-benzoates shown in FIG. 1 (compound Vb$_{1-4}$).

Va wherein K is H, OH, and R, B and G are defined above.

Fully protected compounds such as those shown in FIG. 1 can be further extended prior to attaching a modifying moiety to the protecting group. For example, these compounds can be condensed with the 5'-hydroxyl group of a partially protected and assembled oligonucleotide, either in solution or by solid phase methods, to prepare fully protected oligonucleotides having a reactive linking group(s) (L) on the protecting group (P). The protecting group, which bears the reactive linking group(s) (L), is thereby attached to the 5'-hydroxyl terminus of the oligonucleotide.

Protected compounds of the general formula L—P—C* can be modified at the reactive functionality (L) of the protecting group/linking group P—L. The product of said modification has been previously defined as M—L—P—C*, where M is the modification produced by one or more manipulations at the reactive functional group (L) of the protecting group or any manipulations of an original modification.

In one embodiment, the compound C* is a nucleoside, an oligonucleotide or a nucleic acid and the protecting group/linking group moiety P—L is a triphenylmethyl derivative of formula IIIa. In another embodiment, compound C* is a support bound oligonucleotide attached to a 4,4'-dimethoxysubstituted triphenylmethyl protecting group/linking group P—L (preferred embodiment of the general formula IIIb) by an acid labile ether bond. M is a group as previously defined.

Compounds of the general formula M—L—P—C*, can be deprotected to generate C* and the biproduct M—L—P. In the case where C* is an oligonucleotide, it is possible to further manipulate compound C* of the complex M—L—P—C*. In one embodiment, the C* is a fully protected and support bound oligonucleotide, P—L is a heterobifunctional triphenylmethyl derivative of the general formula IIIa (the oligonucleotide is protected by P as an acid cleavable ether), and M is a modifying moiety which can include but is not limited to the groups previously described and which may or may not be protected. The complex M—L—P—C* can be cleaved from the support and partially deprotected using methods commonly employed in oligonucleotide synthesis. In a final step, the modified protecting group linker P—L, can be removed to generate a fully deprotected oligonucleotide and a biproduct having the general formula M—L—P.

Partially protected oligonucleotides can undergo several other manipulations prior to complete deprotection. These include further manipulations of M and/or immobilization of the oligonucleotide to a support via the modification M. In a preferred embodiment, P—L is a heterobifunctional triphenylmethyl derivative of the general formula IIIa (the oligonucleotide is protected by P as an acid cleavable ether), and M is a hydroxyalkyl moiety, a carboxyalkyl moiety, an aminoalkyl moiety or a thioalkyl moiety. In another preferred embodiment, C* is a partially protected oligonucleotide, P—L is a heterobifunctional triphenylmethyl derivative of the general formula IIIb (the oligonucleotide is protected by P as an acid cleavable ether), and M is an aminoalkyl moiety.

According to the method, an oligonucleotide can-be labeled via the hydroxyl group, carboxyl group, amino group or thiol group of the modification M. Suitable detection labels include a radioisotope, fluorophore, luminescent compound or chemiluminescent compound, biotin, an affinity or purification handle (such as long alkyl chains or polymers) or a biologically active molecule (such as a peptide, a protein, a nucleoside, a nucleotide, an oligonucleotide, a nucleic acid, a monosaccharide, an oligosaccharide, steroid, lipid, alkaloid or a carbohydrate). Preferably, the detection label is biotin or a fluorophore.

The complex M—L—P—C* can also be immobilized onto a support via M. For example, M can be a carboxyalkyl moiety, an aminoalkyl moiety or a thioalkyl moiety. The carboxyl moiety of the complex (where M is a carboxyalkyl moiety) can be activated by a water soluble carbodiimide and coupled to a support containing nucleophiles. Likewise, the amino-containing complex (where M is an aminoalkyl) can be covalently immobilized to supports containing electrophilic chemical functional groups, such as isothiocyanate, isocyanate, acyl halide, sulfonyl halide, acyl imadozolide, acyl N-hydroxysuccinimide, alkyl halide and active ester containing supports. The thiol-containing complex (where M is a thioalkyl moiety) can be immobilized by reaction with the above-described chemically reactive supports or by passing it over a commercially available mercury containing support as has been previously described for thiol-containing oligonucleotides (Blanks, B. et al., *Nucl. Acids. Res.* 16:10283–10299 (1988)).

An advantage to immobilization of a complex containing the triphenylmethyl protecting group/linking group P—L to a support is that products can be selectively adsorbed to the support and subsequently cleaved from the protecting group. Upon adsorption of the complex, all unbound impurities can be washed from the support. Compound C* can then be removed from the support in pure form under conditions in which the complex M—L—P remains immobilized (adsorbed) to the support.

In a preferred embodiment, M is biotin attached to the triphenylmethyl protecting group/linking group (P—L) via a spacer molecule, such as an alkyl chain. Attachment of biotin to M of the protected oligonucleotide can occur after partial deprotection and cleavage from the solid support; however, it is preferable to perform the biotinylation while the oligonucleotide is support bound. The resulting biotinylated complex can be efficiently immobilized to a commercially available avidin or streptavidin support as has been previously described (Coull, J. M. et al., *Tett. Lett.* 27:3991–3994 (1986)).

In one embodiment of this invention, two or more compounds of interest can be simultaneously separated and purified from a mixture comprising two or more compounds of interest and impurities, and from each other. This purification method is herein referred to as multiplex purification. According to the method, compounds of the general formula L—P—C* can be prepared as previously described. For illustration purposes, C* can be defined as a fully protected oligonucleotide A (L—P—A), and a fully protected oligonucleotide B (L—P—B). Preferably, the protecting group/linker P—L is a triphenylmethyl derivative of the general formula IIIa (the oligonucleotide is protected by P as the 5' terminal trityl ether). While support bound, the reactive site L of the 5'-terminal protecting group P of each of the fully protected oligonucleotides (L—P—A and L—P—B) can be further modified. For simplicity, the modifications are defined as $M_1$ and $M_2$ respectively, so as to prepare compounds of the general formula $M_1$—L—P—A and $M_2$—L—P—B. $M_1$ and $M_2$ are affinity or purification handles having an affinity for a support S, such as alkyl chains of differing carbon lengths. Preferably, the affinity or purification handle $M_2$ should have a significantly greater affinity for the support S than does the affinity or purification handle $M_1$. In the optimal case, the modification $M_2$ is a significantly longer alkyl chain than is the modification $M_1$. Additionally, the components of the mixture and compounds A and B should have little or essentially no affinity for the support S.

Reversed phase high performance liquid chromatography (HPLC) is typically used for the purification of partially protected oligonucleotides. In principle, the triphenylmethyl group of the partially protected and fully assembled products will interact more strongly with the hydrophobic stationary phase (commonly C18 coated silica) than do the impurities. The terminated sequences and other impurities will, therefore, elute quickly from the column so that the partially protected oligonucleotide product will be well separated and can be collected as it elutes from the column. See McLaughlin, L. W. and Piel, N., *Oligonucleotide Synthesis, A Practical Approach* (1984), Gait, M. J. (ed) IRL Press Inc., Oxford, England, pp. 199–218.

When the mixture comprising and partially protected oligonucleotides $M_1$—L—P—A and $M_2$—L—P—B and impurities, is subjected to reversed phase HPLC separation conditions, the components will elute in their respective order and can be collected, each in purified form. Once separated, the protecting groups can be removed to generate the fully protected and purified oligonucleotides A and B and the biproducts of general formula P—L—$M_1$ and P—L—$M_2$.

Compounds of this invention can also be used in polymerase catalysed extension reactions. According to the method, an oligonucleotide (e.g., 10–30 nucleotides in length) is prepared such that it is complementary to and, therefore, will hybridize to, a single-stranded nucleic acid template. Once hybridization occurs, a DNA polymerase will extend the primer using the nucleic acid as a template to prepare the complementary nucleic acid sequence. Labeled primers can be used in polymerase catalyzed extension reactions provided that they are not inhibited from annealing to a template by virtue of the attached label and provided that the functional group from which the extension reaction proceeds is not made inaccessible by the incorporation of the label. A preferred variation of the polymerase extension reaction is the polymerase chain reaction (PCR; U.S. Pat. 4,683,202). Polymerase catalyzed primer extension reactions of the 3'-terminal hydroxyl group can also be performed.

The product of a primer extension reaction can be manipulated by any of the previously described methods. For example, if the modification M is a detection label, it is possible to detect the complex by an appropriate means, such as by fluorescence, radio-labeling chemiluminescence, or luminescence. If the complex is an affinity handle such as biotin, it is possible to immobilize it to an avidin or streptavidin support. The completely unmodified double-stranded product can likewise be generated at any time by removal of the protecting group. Additionally, a double-stranded DNA product of nucleic acid synthesis can be denatured to prepare single stranded DNA.

The polymerase chain reaction requires two primers which are complementary to different strands of a nucleic acid template and flank the region of the template to be amplified. As with any primer extension reaction, the product of PCR is a double-stranded nucleic acid. Modified oligonucleotide primers of the general formula M—L'P—C* can be used as amplification primers in the PCR process. Partially protected double-stranded nucleic acids generated by primer extension can be further modified according to the methods previously described. If two (2) labeled oligonucleotide primers are used in the polymerase chain reaction, the double-stranded product will contain labels on the 5' ends of the different strands. This product can also undergo all the same reactions described herein for any partially protected oligonucleotide, including condition dependent removal of the protecting groups to generate an unmodified double stranded nucleic acid.

The invention will be further illustrated by the following non-limiting Examples.

EXAMPLE 1

Synthesis of 2-[4-(bis-(4-methoxyphenyl)-hydroxymethyl)-phenyl]-4,4-dimethyloxazoline To 350 mmol of 2-(4-bromophenyl)-4,4-dimethyl-1,3-oxazoline (A. I. Meyers et al., *J. Amer. Chem. Soc.* 92: 6646–6647 (1970)) dissolved in 1 liter of freshly distilled tetrahydrofuran was added 17.0 g (700 mmol) of magnesium. The solution was warmed until the reaction initiated and thereafter was heated gently for 1 hr. An extra one liter of tetrahydrofuran was added at this time. 345 mmol of 4,4′-dimethoxy-benzophenone was added and the coupling reaction stirred for 2 hrs at gentle reflux. The reaction was filtered and concentrated to approximately 500 ml. The solution was poured slowly into a flask containing 8% aqueous $KHSO_4$ (1L) and diethyl ether (1L). The layers were separated and the organic fraction was washed once with $H_{20}$, dried ($MgSO_4$), filtered and evaporated to yield 147.2 g of orange oil. The purified product was obtained by crystallization from benzene or ethyl acetate. 105.4 g (252 mmol, 73%) lt. green crystal mp. 140°–142° C. $^1$H-NMR ($CDCl_3$): $\delta$=1.36 (s, 6H, —$CH_3$); 2.82 (s, 1H, O—H); 3.79 (s, 6H, —$OCH_3$); 4.09 (s, 2H, $CH_2$); 6.80–7.17 (dd, 8H, $CH_3O$—Ar—H); 7.32–7.89 (dd, 4H, oxaz—Ar—H)

EXAMPLE 2

Synthesis of 4-carboxy-4′,4″-dimethoxytriphenylhydroxymethane (FIG. 1; Compound Ib)

To 200 mmol of 2-[4-(bis-(4-methoxyphenyl)-hydroxymethyl)-phenyl]-4,4-dimethyloxazoline was added 400 ml of 80% aqueous acetic acid and the solution was stirred at 60°–70° C. for 6–7 hrs. The product was concentrated to an orange oil and redissolved in 500 ml of 20% NaOH in ethanol/water, 1/1 (v/v). This solution was refluxed vigorously for one hour and then concentrated to a white semi solid. The residue was dissolved in 1 L of $H_2O$ and acidified with 3M HCl to pH 1.0. The solid was filtered off and dissolved 750 ml of ethyl acetate. This solution was washed two times with dilute acid, dried ($MgSO_4$) filtered and evaporated to yield 81.2 g of an orange foam. The crystalline product was obtained from benzene. 67.49 g (185 mmol, 93%) orange crystalline solid mp. 105°–107° C. $^1$H-NMR ($CDCl_3$): $\delta$=3.80 (s, 6H, $OCH_3$); 6.80–7.20 (dd, 8H, $CH_3O$—Ar—H); 7.42–8.06 (dd, 4H, HOOC—Ar—H)

EXAMPLE 3

Synthesis of N-succinimidyl-4-[bis-(4-methoxyphenyl)-hydroxymethyl]-benzoate (FIG. 1: Compound IIb)

To 6 mmol of Ib and 9 mmol of N-hydroxysuccinimide (NHS) in 10 ml of ethyl acetate stirring at 0° C. was added 7.5 mmol of N,N′-dicyclohexylcarbodiimide (DCC). The reaction was stirred at 0° C. for 2 hrs, then an additional 0.5 mmol of DCC and 1 mmol of NHS was added. After 4.5 hrs at 0° C. the reaction was filtered and diluted with ethyl acetate to a volume of 50 ml. This solution was washed with water four times, 5% aqueous $NaHCO_3$ once and again with water. The organic layer was dried ($MgSO_4$), filtered and evaporated to yield 70.0 g of yellow foam. The purified product was obtained by crystallization from ethyl acetate. 2.01 g (4.4 mmol, 73%) white solid (two crystalline forms) mp. 168°–170° C. or 186°–188° C. $^1$H-NMR ($CDCl_3$): $\delta$=2.77 (s, 1H, O—H); 2.90 (s, 4H, $CH_2$); 3.81 (s, 6H, $OCH_3$); 6.82–7.17 (dd, 8H, $CH_3O$—Ar—H); 7.48–8.10 (dd, 4H, succinimidyl-Ar—H)

EXAMPLE 4

Synthesis of N-succinimidyl-4-[bis-(4-methoxyphenyl)-chloromethyl]-benzoate (FIG. 1: Compound IIIb)

To 50 mmol of IIb was added 250 ml of acetyl chloride. The solution was boiled for three hours and cooled. 350 ml of anhydrous diethyl ether was added and the mixture was placed overnight at 5° C. The white crystalline product was collected by vacuum filtration. 21.35 g (44.5 mmol, 89%) white crystalline solid mp. 203°–204° C. $^1$H-NMR ($CDCl_3$): $\delta$=2.91 (s, 4H, $CH_2$); 3.82 (s, 6H, $OCH_3$); 6.81–7.17 (dd, 8H, $CH_3O$—Ar—H); 7.42–8.10 (dd, 4H, succinimidyl-Ar—H)

EXAMPLE 5

General procedure used to prepare N-succinimidyl-4-[bis(4-methoxyphenyl)-5′-O-(2′-deoxynucleosidyl)-methyl]-benzoates (FIG. 1: Compounds $IVb_{1-4}$)

To 7 mmol of suitably protected 2′-deoxynucleoside which had been dried by coevaporation from pyridine was added dropwise a solution containing 8 mmol of IIIb dissolved in 25 ml pyridine. The reaction was stirred until complete (3–12 hrs) and quenched by the addition of 1 ml of methanol. The solvent was removed and the residue partitioned between 50 ml of ethyl acetate and 50 ml of 5% aqueous $NaHCO_3$. The organic layer was washed with another portion of 5% aqueous $NaHCO_3$ and once with $H_2O$ prior to being dried ($MgSO_4$), filtered and evaporated. The final product was obtained by crystallization from the described solvent.

$IVb_1$. 4.34 g (6.3 mmol, 90%) white crystal (benzene) $^1$H-NMR ($CDCl_3$): $\delta$=1.58 (d, 3H, $CH_3$); 2.20–2.47 (m, 2H, H2′,H2″); 2.64 (s, 1H, O-H); 2.88 (s, 4H, $CH_2$); 3.30–3.45 (m, 2H, H5,H5″); 3.79 (d, 6H, $OCH_3$); 4.04–4.09 (m, 1H, H4′); 4.52 (m, 1H, H3′); 6.36 (dd, 1H, H1′); 6.83–6.87 (dd, 4H, Ar—H); 7.23–7.30 (dd, 4H, Ar—H); 7.44 (d, 1H, H6); 7.58–7.62 (d, 2H, Ar—H); 8.04–8.08 (d, 2H, Ar—H); 8.87 (s, 1H, N—H)

$IVb_2$. 3.08 g (3.9 mmol, 55%) opaque solid (toluene) $^1$H-NMR ($CDCl_3$): $\delta$=2.51–2.63 (m, 1H, H2′); 2.85 (s, 4H, $CH_2$); 2.89–3.03 (m, 1H, H2″); 3.32–3.47 (m, 2H, H5′,H5″); 3.78 (d, 6H, $OCH_3$); 4.17–4.23 (m, 1H, H4′); 4.69–4.76 (m, 1H, H3′); 6.44–6.50 (t, 1H, H1′); 6.78–6.86 (m, 4H, Ar—H); 7.12–7.29 (m, 5H, Ar-H); 7.48–7.60 (m, 4H, Ar—H); 7.94–8.06 (m, 4H, Ar—H); 8.14 (s, 1H, H8); 8.70 (s, 1H, H2); 9.15 (s, 1H, N—H) $IVb_3$. 3.34 g (4.3 mmol, 62%) opaque solid (toluene) 1H-NMR ($CDCl_3$): $\delta$=2.19–2.32 (m, 1H, H2′); 2.67–2.79 (m, 1H, H2″); 2.87 (s, 4H, $CH_2$); 3.42–3.52 (m, 2H, H5′,H5″), 3.81 (d, 6H, $OCH_3$); 4.15–4.19 (m, 1H, H4′); 4.47–4.55 (m, 1H, H3′); 6.23–6.29 (t, 1H, H1); 6.86–6.92 (m, 4H, Ar—H); 7.19–7.32 (m, 5H, Ar—H); 7.50–7.62 (m, 5H, Ar—H); 7.86–7.90 (m, 2H, Ar—H); 8.04–8.09 (m, 2H, At—H); 8.18 (d, 1H, H6) $IVb_4$. 4.16 g (5.3 mmol, 76%) white crystal (ethyl acetate) $^1$H-NMR (DMSO-$d_6$): $\delta$=1.12 (d, 6H, $CH_3$); 2.30–2.42 (m, $^1$H, H2′); 2.70–2.84 (m, 2H, CH, H2″); 2.88 (s, 4H, $CH_2$); 3.10–3.27 (m, 2H, H5′,H5″); 3.72 (d, 6H, $OCH_3$); 3.96 (m, 1H, H4′);4.42 (m, 1H, H3′); 5.36 (d, 1H, O—H); 6.27 (t, 1H, H1′); 6.76–6.87 (dd, 4H, Ar—H); 7.18–7.23 (dd, 4H, Ar—H); 7.60 (d, 2H, Ar—H); 7.97 (d, 2H, Ar—H); 68.15 (s, 1H, H8)

EXAMPLE 6

General procedure for the preparation of N-succinimidyl-4-[bis-4-(methoxyphenyl)-5'-O-(3'-O-(N,N-diisopropyl-amino-2-cyanoethylphosphinyl)-2'-deoxynucleosidyl)-methyl]-benzoates (FIG. 1; Compounds $Vb_{1-4}$)

To 3 mmol of the appropriately protected monomer ($IVb_{1-4}$) dissolved in 15 ml of tetrahydrofuran, was added 12 mmol of diisopropylethylamine and 3.3 mmol of 2-cyanoethyldiisopropylaminochlorophosphine. The reaction was stirred at ambient temperature for 1-2 hrs, filtered and concentrated. The residue was dissolved in 100 ml of ethyl acetate, washed 3 times with 10% aqueous $Na_2CO_3$, dried ($Na_2SO_4$) filtered and evaporated. The product was dissolved in 15 ml of ethyl acetate and dripped into 250 ml of hexanes. The precipitate was collected and dried.

$Vb_1$. 2.10 g (2.4 mmol, 79%) $^{31}$P-NMR ($CDCl_3$): $\delta = 145.550, 145.630$ PPM $Vb_2$. 2.53 g (2.5 mmol, 84%) $^{31}$P-NMR ($CDCl_3$): $\delta = 145.494, 145.677$ PPM $Vb_3$. 1.93 g (2.0 mmol, 66%) $^{31}$P-NMR ($CDCl_3$): $\delta = 145.604, 145.820$ PPM $Vb_4$. 2.46 g (2.5 mmol, 84%) $^{31}$P-NMR ($CDCl_3$): $\delta = 144.478, 145.519$ PPM

EXAMPLE 7

Oligonucleotide synthesis

Oligonucleotides were assembled from commercially available 2-cyanoethylphosphoramidites either manually (Example 7a) or with an automated synthesiszer. A prototype large scale DNA synthesizer at 30 $\mu$mol scale was used in Example 7b whereas a Milligen/Biosearch Model 7500 DNA synthesizer running the standard 1 $\mu$mol protocol was used in Example 9. In all cases, the final condensation was performed with the appropriate modified trityl protected 2-cyanoethylphosphoramidite ($Vb_{1-4}$) to yield fully protected, support bound oligonucleotides having a 5'-terminal NHS ester linking group (L). The resins (or portions of the resins) were treated with amino group(s) containing compounds to functionalize the 5'-terminal NHS ester linking group (L) according to Example 8. Further extension or labeling could be performed on resin bound fully protected 5'-functional group containing oligonucleotides according to the method described in Example 9 or the oligonucleotides could be removed from the support, partially deprotected, and reacted in solution according to Example 11.

EXAMPLE 7a

Synthesis of a thymidine dimer at 15 $\mu$mol scale

A commercially available 15 $\mu$mol DMT-Thymidine-Succinyl-AP-CPG resin (Milligen/Biosearch, Division of Millipore, Burlington, Mass.) was detritylated with 3% dichloroacetic acid in dichloromethane until the eluent was colorless. The resin was washed with 5 ml of acetonitrile and dried under high vacuum. The resin was washed again with 5 ml of dry acetonitrile and then 950 $\mu$l of 0.085M thymidine phosphoramidite ($Vb_1$ in FIG. 1) in dry acetonitrile and 2 ml of commercially available tetrazole activating solution were mixed and slowly pushed through the resin over a period of four minutes. The resin was washed with 5 ml of acetonitrile and then 6 ml of commercially available $I_2$ oxidation solution was pushed through the column over a period of two minutes. Finally the resin was washed with 5 ml of acetonitrile and dried under high vacuum. Portions of the resin were treated with amino group(s) containing compounds to functionalize the 5'-terminal NHS ester linking group (L) according to Example 8. The 5'modified oligonucleotides were then partially deprotected and removed from the support according to Example 10. Table 1 summarizes the various compounds reacted with L and the yield of product as determined by HPLC analysis of the crude 5'-modified thymidine dimer.

TABLE 1

Amino group(s) containing compounds used to modify the 5'-terminal NHS ester linking group (L) of the thymidine dimer.

| Amine | Retention Time* | Area % |
|---|---|---|
| cyclohexylamine | 40.37 | 99+ |
| 1-aminohexane | 43.02 | 99+ |
| 1,3-diaminopropane | 29.15 | 78.5 |
| 1,4-diaminobutane | 29.60 | 73.3 |
| 1,6-diaminohexane | 31.24 | 73.0 |
| 1,8-diaminooctane | 33.88 | 70.3 |
| 1,12-diaminododecane | 40.78 | 71.0 |
| 3-amino-1,2-propanediol | 29.85 | 99+ |
| 2-amino-1,3-propanediol | 27.81 | 72.0 |
| 6-aminohexanol | 34.43 | 99+ |
| 6-aminocaproic acid | 30.83 | 91.9 |

*Reversed-phase HPLC analysis: Delta Pak C18-100A Liquid Chromatography Column (Waters Division of Millipore) Buffer A = 100 mM triethylammonium acetate pH 6.8, Buffer B = 95/5 acetonitrile/water Gradient: 0 min.(5% B); 50 min.(60% B); Flow rate = 1.0 ml/min; Temperature 40° C.

EXAMPLE 7b

Synthesis of 5'-TCCCAGTCACGACGT-3' at 30 $\mu$mol scale

A 30 $\mu$mol synthesis of 5'-TCCCAGTCACGACGT-3' was conducted using a prototype large scale DNA synthesizer running the protocol described in Table 2. The final condensation reaction was performed using compound $Vb_1$ to introduce the reactive NHS ester linking group (L) at the 5' terminus of the support bound oligonucleotide.

At the end of the synthesis a portion of the resin was treated with 1,6-diaminohexane according to Example 8. The amine functionalized oligonucleotide was removed from the resin and partially deprotected as described in Example 10. Solution phase reaction of the 5'-terminal amino group with N-hydroxysuccinimidyl-biotin is described in Example 11.

The remainder of the resin was treated with various alkyl amines according to Example 8. The partially protected 5'-modified oligonucleotides were obtained by treating the resins according to Example 10 and were used to demonstrate multiplex purification in Example 13.

TABLE 2

Large scale DNA synthesis protocol.

| Function | Infuse Rate (ml/min) | Duration (sec) |
|---|---|---|
| DCA wash | 7000 | 240 |
| ACN wash | 7000 | 120 |
| TEA wash | 7000 | 60 |
| ACN wash | 7000 | 300 |
| Condensation | N/A* | 300 |
| ACN wash | 7000 | 240 |
| $I_2$ oxidation | 7000 | 30 |

TABLE 2-continued

Large scale DNA synthesis protocol.

| Function | Infuse Rate (ml/min) | Duration (sec) |
|---|---|---|
| ACN wash | 7000 | 180 |

*For each condensation reaction a tenfold excess of 2-cyanoethylphosphoramidite is dissolved in enough 2.5% 1H-tetrazole in acetonitrile (w/v) to prepare a 200 mM solution. The activated amidite is infused and recirculated through the column bed for the period indicated.

EXAMPLE 8

Aminolysis of the N-hydroxysuccinimidyl ester (Linker Group L) with alkylamines, alkyldiamines, hydroxyalkyl amines or carboxyalkyl amines After the solid phase chemical assembly of an oligonucleotide, the support was placed in vacuo to remove any residual solvent. Typically, 2 ml of a 0.5–1.0M solution of amino group(s) containing compound in 75% aqueous dioxane was pushed through the resin over a period of two minutes. Compounds not soluble in 75% aqueous dioxane were dissolved as described in Table 3. The support was then washed with 2 ml of tetrahydrofuran and 2 ml of acetonitrile. The resin was subsequently dried in vacuo and was treated with ammonia as described in Example 10 or reacted further as demonstrated in Example 9. Reversed phase high performance liquid chromatographic (HPLC) analysis was used to determine the purity of all crude partially protected products. All analytical separations were performed with a 3.8 mm ×150 nun Delta Pak C18-100A chromatography column.

TABLE 3

Variations on conditions used to derivatize NHS esters.

| Amine | Solvent | Concentration |
|---|---|---|
| 1-aminododecane | THF* | 1.0 M |
| 1-aminopentadecane | THF | 0.5 M |
| 1-aminooctadecane | THF | 0.4 M |
| 1,8-diaminooctane | 9/1 THF/water | 1.0 M |
| 1,12-diaminododecane | 95/5 dioxane/water | 0.5 M |
| 6-aminocaproic acid | 1/1 dioxane/5% aqu.NaHCO$_3$ | 0.5 M |

*THF is an abbreviation for tetrahydrofuran

EXAMPLE 9

Support bound synthesis of biotin and fluorescein labeled PCR primers

Two oligonucleotides complementary to opposite strands of a bacteriophage lambda DNA were chemically assembled according to Example 7. The sequences prepared were 5'-GATGAGTTCGTGTCC-GTACAACTGG-3'and 5'-GGTTATCGAAAT-CAGCCACAGCGCC-3'. These oligonucleotides would serve as primers for the amplification of a 500 bp segment of lambda DNA using the polymerase chain reaction (PCR)(Example 15) and are referred to as PCR Primer 1 and PCR Primer 2, respectively.

After completion of the 1 μmol synthesis of each primer the 5'-terminal NHS ester of the resin bound protected oligonucleotides was reacted with 1,12-diaminododecane as described in Example 8. Both resins were then split into three unequal portions.

One half of the resin from each synthesis was dried under high vacuum and treated with ammonia according to Example 10. Both crude samples were purified according to the method described in Example 12 and a portion of each purified sample was detritylated according to the method described in Example 14. This produced both the completely deprotected and purified PCR primers (hereafter referred to as Control PCR Primer 1 and 2 respectively) required for Example 17. Each sample was shown to be pure by reversed-phase HPLC analysis One quarter of the remaining resin from each primer synthesis was exposed to one milliliter of a 0.25M solution of N-hydroxysuccinimidyl-biotin dissolved in dimethylformamide/diisopropylethylamine/water, 7/2/1 (v/v/v) for a period of 30 minutes. Similarly, the remaining one quarter of the resin from each primer synthesis was exposed to one milliliter of a 0.125M solution of di-O-pivaloyl-5-(N-succinimidyl)-fluorescein dissolved in dioxane/diisopropylethylamine/water, 7/2/1 (v/v/v) for a period of 60 minutes. Once the labeling reactions were complete, the support was washed with 2 ml of dimethylformamide, 2 ml of tetrahydrofuran, 2 ml of acetonitrile and finally dried under high vacuum. Partially protected labeled oligonucleotides were obtained by treatment of the resins containing the fully protected and labeled oligonucleotides according to Example 10.

Figure 2:
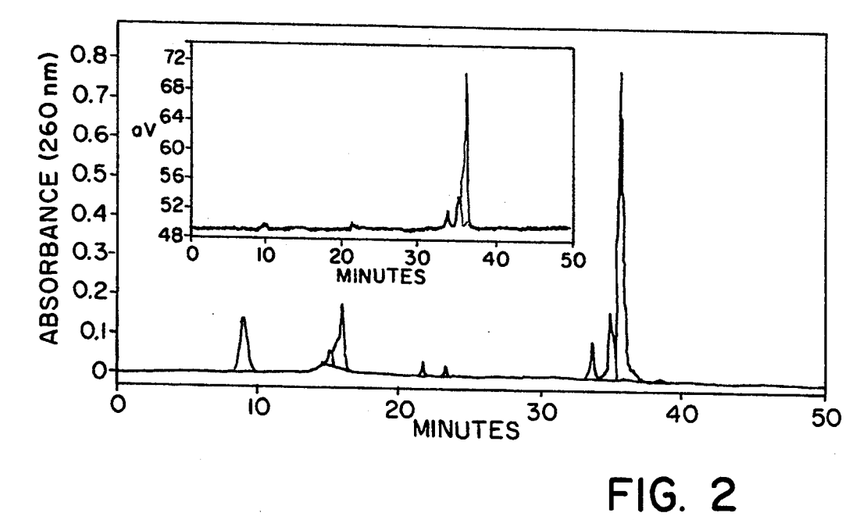
FIG. 2 is an high performance liquid chromatography (HPLC) analysis of crude partially protected fluorescein labeled polymerase chain reaction (PCR) primer 1.

FIG. 2 is the HPLC analysis of the crude partially protected fluorescein labeled PCR Primer 1. Both ultraviolet absorbance at 260 nm and fluorescence (inset) at 470 nm (410 nm exitation wavelength) were recorded. The analysis shows that the major component eluting at 34.4 minutes is the only fluorescent product. The crude sample was purified according to the method described in Example 12 and is hereafter referred to as Fluor-PCR Primer 1. HPLC analysis of the crude sample of fluorescein labeled PCR Primer 2 (hereafter called Fluor-PCR Primer 2) was similar to that observed for Fluor-PCR Primer 1. It was similarly purified by reversed-phase HPLC.

Reversed phase HPLC analysis of the crude biotin labeled Control PCR Primers (hereafter referred to as Bio-PCR Primer 1 and 2, respectively) was also very similar. The major component of each sample was isolated by the method described in Example 12. The presence of biotin in the oligonucleotides was confirmed by the binding of the purified products to a streptavidin agarose support (Coull, J. M. et al, Tet. Lett. 27:3991–3994 (1986)). Bio-PCR Primer 1 and BioPCR Primer 2 were used in polymerase chain reactions as described in Example 17.

The HPLC conditions were:
Buffer A=100 mM triethylammonium acetate pH 6.8; Buffer B=95:5 acetonitrile/water; Gradient: 0 min (5% B), 50 min (60% B); Flow rate=1.0 ml/min; Temperature: 40° C.

EXAMPLE 10

Partial deprotection and removal of oligonucleotides from solid supports

Once the oligonucleotide was functionalized/labeled as desired, the dried resin was treated with 0.5 ml of concentrated ammonia at 55° C. for 8–10 hrs. The resin was removed by filtration and washed with water. The filtrate and washings were combined and concentrated to dryness. The crude oligonucleotide was dissolved in 1 ml of deionized water. The yield and concentration of oligonucleotide were estimated from the absorbance at 260 nm of 10 μl of the sample diluted to 1.0 ml with water.

EXAMPLE 11

Solution phase labeling of oligonucleotides

Labeled oligonucleotides were also be obtained by the solution phase reaction of functional group containing partially protected oligonucleotides. The oligonucleotide 5'-TCCCAGTCACGACGT-3' was prepared according to Example 7b and treated with 1,6-diaminohexane to functionalize the NHS ester linking group L according to the method described in Example 8. After cleavage and partial deprotection of the oligonucleotide according to the method described in Example 10, the 5'-terminal amino group of the partially deprotected oligonucleotide was biotinylated as follows:

To 16 milligrams of N-hydroxysuccinimidyl-biotin dissolved in 500 μl of dimethylformamide was added 250 μl of 0.1M 4-(2-hydroxyethyl)-1-piperazine-ethanesulfonic acid (HEPES) pH 7.7 and 50 $A_{260}$ units of crude 5'-amino group containing partially protected 15-mer in 250 μl of water. Aliquots of the reaction mixture taken at 5 minutes, 55 minutes and 120 minutes were analyzed by reversed-phase HPLC. The analysis indicated complete disappearance of the major component of the crude mixture in favor of a more hydrophobic product within two hours. No other components of the mixture were observed to react within two hours. This new product was isolated by preparative scale reversed-phase HPLC according to the method described in Example 12 and was shown to bind to streptavidin agarose (Coull, J. M. et al. Ibid).

The HPLC elution conditions were:
Buffer A=100 mM triethylammonium acetate pH 6.8; Buffer B=95:5 acetonitrile/water; Gradient: 0 min (5% B), 40 min (40% B); Flow rate=1.0 ml/min; Temperature: 40° C.

EXAMPLE 12

Preparative purification of partially protected oligonucleotides

Oligonucleotides were purified by preparative scale HPLC. Separations were achieved using a 7.8 mm×300 mm Delta Pak C18-300A Liquid Chromatography Column (Waters, Milford Mass.). The column eluent was collected in approximately one milliliter fractions in tubes containing 50 μl of diisopropylethylamine and 50 μl of unbuffered 20 mM tris (hydroxymethyl)aminomethane (Tris). Product fractions were concentrated to dryness under vacuum, the residue was dissolved in sterile water and the contents of the tubes combined. The material was again concentrated to dryness, and the residue dissolved in sterile water. Aliquots of samples to be used in polymerase chain reactions were adjusted to a concentration of 20 nmol/mL. Elution conditions for preparative HPLC separations were optimized for individual isolations.

EXAMPLE 13

Multiplex purification of partially protected oligonucleotides

Multiplex purification was defined as the simultaneous purification of two or more compounds. Since it is possible to manipulate the 5'-terminus of a fully protected oligonucleotide as described in Example 8, it is also possible to predetermine the affinity of the resulting partially protected oligonucleotide for an affinity support. Attachment of alkyl chains to the triphenylmethyl derivative results in selective alterations to the affinity of the partially protected oligonucleotides for hydrophobic supports. The common support used in preparative scale reversed-phase high performance liquid chromatography (HPLC) is C18 coated silica for which oligonucleotides have little affinity.

Figure 3:
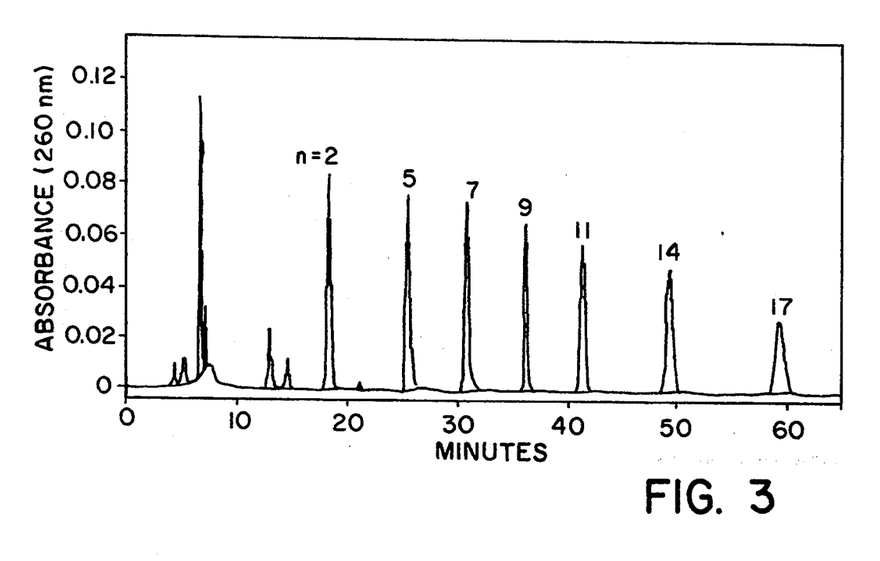
FIG. 3 is is a reversed phase HPLC analysis of a crude mixture comprising seven partially protected oligonucleotides.

The effect of alkyl chain length on the retention of partially protected oligonucleotides is demonstrated. In this example, portions of the resin containing the fully protected sequence 5'-TCCCAGTCACGACGT-3'(from Example 7b) were treated by the method described in Example 8 with seven different alkylamines of general formula $H_2N(CH_2)_nCH_3$ where n=2, 5, 7, 9, 11, 14, or 17. The resin aliquots were mixed and treated with ammonia as described in Example 10. FIG. 3 is the reversed-phase HPLC analysis of the components of the crude mixture. Each of the seven partially protected oligonucleotides was baseline separated from the others by several minutes and the products eluted in order of increasing alkyl chain length. The identity of the peaks was confirmed by coelution with independently isolated authentic samples.

The HPLC conditions used were:
Buffer A=100 mM triethylammonium acetate pH 6.8; Buffer B=95:5 acetonitrile/water; Gradient: 0 min (10% B), 5 min (20% B), 50 min (55% B), 60 rain (60% B), 65 min ( 60% B); Flow rate=1.0 ml/min; Temperature: 40° C.

In another example of multiplex purification, two partially protected oligonucleotides of differing length and sequence were simultaneously purified. This was performed by derivatization of the NHS ester linking group (L) of two fully protected oligonucleotides with alkyl chains of differing length according to the procedure described in Example 8. A 30-mer of nucleotide sequence 5'-AATTCATAAGGTAATT-CAAAATGTTTGTCA-3'was treated with 1-aminodecane and a 24-mer of nucleotide sequence 5'-ACTCCCGGCCCCCGGGCCTCCACC-3'was treated with 1-aminohexane. Analytical scale HPLC of the crude partially protected products obtained according to Example 10 was performed. The major component of the 1-aminodecane derivatized 30-mer eluted at 33.8 minutes and comprised 60.6% of the sample as determined by integration of the peak areas. The major component of the 1-aminohexane derivatized 24-mer eluted at 24.0 minutes and comprised 58.8% of the sample as determined by integration of the peak areas. These two major products having significantly different retention times were baseline resolved in a simultaneous preparative scale purification according to Example 12. Removal of the 5'-terminal modified protecting group according to Example 14 gave the purified fully deprotected oligonucleotides whose identity was confirmed by coelution with independantly isolated authentic samples.

The analytical HPLC elution conditions used were:
Buffer A=100 mM triethylammonium acetate pH 6.8; Buffer B=95:5 acetonitrile/water; Gradient: 0 min (10% B), 5 min (20% B), 50 min (55% B), 60 min (60% B), 65 min (60% B); Flow rate=1.0 ml/min; Temperature: 40° C.

The preparative HPLC elution conditions were:
Buffer A=100 mM triethylammonium acetate pH 6.8; Buffer B=95:5 acetonitrile/water; Gradient: 0 min (10% B), 5 rain (20% B), 50 rain (55% B); Flow rate=3.0 ml/min; Temperature: 60° C.

EXAMPLE 14

Complete deprotection of partially protected oligonucleotides

When the complete deprotection of modified trityl containing oligonucleotides was desired, the samples were evaporated to dryness and dissolved in 100 µl of 80% aqueous acetic acid. After two hours at 0° C. the samples were evaporated to dryness and dissolved in a known volume of water.

This procedure was carried out on one half of each of the amino group containing Control PCR primer sequences described in Example 9. This yielded fully deprotected unmodified (natural) primers for the polymerase chain reactions described in Example 17.

Complete removal of the 5'-terminal modified trityl group by the aqueous acid was assayed by reversed phase HPLC. Analysis of the purified partially protected 1,12-diaminododecane modified PCR Primer 1 described in Example 9 indicated a single compound which eluted at 30.7 minutes. Following acid treatment no starting material remained and a single peak corresponding to the fully deprotected oligonucleotide was observed to elute at 15.5 minutes.

The HPLC analysis conditions were:
Buffer A=100 mM triethylammonium acetate pH 6.8; Buffer B=95:5 acetonitrile/water; Gradient: 0 min (5% B), 50 min (60% B); Flow rate=1.0 ml/min; Temperature: 40° C.

EXAMPLE 15

Conditions used for PCR reactions

Polymerase chain reactions (PCR) were comprised of 200 µl of 50 mM KCl, 10 mM buffer (Tris pH 8.3 or N-2-hydroxyethyl piperazine-N'-2-hydroxy propane sulfonic acid (Heppso) pH 8.7 as indicated), 1.5 mM $MgCl_2$ and 200 mM each dNTP containing 10 units of AmpliTaq TM DNA polymerase, 200 pmol each primer, and 2 to 20 fmol bacteriophage lambda DNA template. Two different amplification cycle protocols for 15 repetitions each were used to complete a total of 30 amplification cycles per sample. The cycle for the first 15 repetitions was 15 seconds at 96° C., 15 sec at 65° C. and 30 seconds at 72° C. +2 seconds/cycle extension. The cycle for the second 15 repetitions was 15 seconds at 96° C., 15 sec at 55° C. and 60 seconds at 72° C. +2 seconds/cycle extension.

EXAMPLE 16

Preparation of streptavidin agarose

Streptavidin agarose (Gibco BRL, Bethesda Md.) was treated before use. The agarose was washed three times with 200 µl of 150 mM NaCl, 10 mM $NaH_2PO_4$ pH 7.2 containing 0.05% $NaN_3$ and 10% acetonitrile. A 25 µl aliquot of 0.5M NaCl in 80% aqueous acetic acid containing 0.5% (w/v) aminoethanethiol hydrochloride was then washed through the resin and then 100 µl of this solution was allowed to react with the streptavidin agarose for 1 hr. The resin was again washed three times with 100 µl of 150 mM NaCl, 10 mM $NaH_2PO_4$ pH 7.2 containing .05% $NaN_3$ and 10% acetonitrile.

EXAMPLE 17

Affinity purification and isolation of PCR amplified nucleic acids

The use of 5'-modified oligonucleotides for the purification of polymerase chain reaction products was demonstrated. A 500 base pair segment of bacteriophage lambda DNA was amplified using various combinations of biotinylated or natural (unmodified) primers. Amplification products from reactions containing the biotinylated primers were demonstrated to be selectively retained by a streptavidin agarose support. Exposure of the support to conditions known to cleave the 5'-biotinylated trityl group from the DNA allowed recovery of the 500 base pair fragment in its unmodified form. PCR reactions were carried out as described in Example 15 using the Control PCR Primers 1 and 2 and Bio-PCR Primers 1 and 2 from Example 9. Table 4 describes the various combinations of primers and conditions used in the individual reactions.

TABLE 4

| Primers and conditions used for PCR reactions. | | | |
|---|---|---|---|
| Reaction | Primers | Buffer | Polymerase |
| 1 | Control PCR Primer 1 Control PCR Primer 2 | Tris | — |
| 2 | Control PCR Primer 1 Control PCR Primer 2 | Heppso | — |
| 3 | Control PCR Primer 1 Control PCR Primer 2 | Tris | + |
| 4 | Control PCR Primer 1 Control PCR Primer 2 | Heppso | + |
| 5 | Bio-PCR Primer 1 Control PCR Primer 2 | Heppso | + |
| 6 | Control PCR Primer 1 Bio-PCR Primer 2 | Heppso | + |
| 7 | Bio-PCR Primer 1 Bio-PCR Primer 2 | Heppso | + |

Following amplication, a portion of each PCR reaction (50 µl) was incubated with pretreated (see Example 16) streptavidin agarose (100 µl) for 30 minutes. At the end of the incubation, the supernatant was removed and the streptavidin agarose was washed twice with 100 µl of 150 mM NaCl, 10 mM $NaH_2PO_4$ pH 7.2 containing 0.05% $NaN_3$ and 10% acetonitrile (hereafter called streptavidin buffer).The washings were combined with the supernatant. These samples are the "support eluent" and contain any material which does not bind to the streptavidin support. The streptavidin agarose was again washed twice with 100 µl streptavidin buffer and these aliquots were discarded.

Material that had bound to the streptavidin agarose by the biotin trityl linker was then recovered by exposure of the support to acid. A 25 µl aliquot of 0.5 M NaCl in 80% aqueous acetic acid was washed through the resin bed and saved. The resin was then treated for 2 hours with 100 µl of 0.5M NaCl in 80% aqueous acetic acid at 4° C. The supernatant was recovered and combined with the initial acid wash. The support was then washed three times with 100 µl of a solution containing 0.25 mM Tris pH 9.0, 0.15 mM NaCl and 0.05% sodium azide (w/v) in water/acetonitrile, 8/2 (v/v). The acid fractions and washings were combined and hereafter are referred to as the "acid eluent" samples. These samples contain material which can be removed from the support by conditions known to cleave the trityl ether bond.

To demonstrate that selective adsorption and recovery of biotinylated PCR generated DNA fragments was achieved, the PCR reactions, "support eluent" samples and "acid eluent" samples were analyzed by gel electrophoresis. Prior to the analysis "support eluent" samples and "acid eluent" samples were concentrated to dryness and dissolved in 50 µl of sterile water. Salt and excess primer were removed by applying each sample to a Sephadex G-50 spin column in the manner described by the manufacturer (Boehringer Mannheim, Indianapolis, Ind.). These samples were again evaporated to dryness and dissolved in 50 μl of sterile water. Aliquots of 10 μl were then applied to a 2% agarose electrophoretic gel and compared directly with PCR reaction products.

Figure 4:
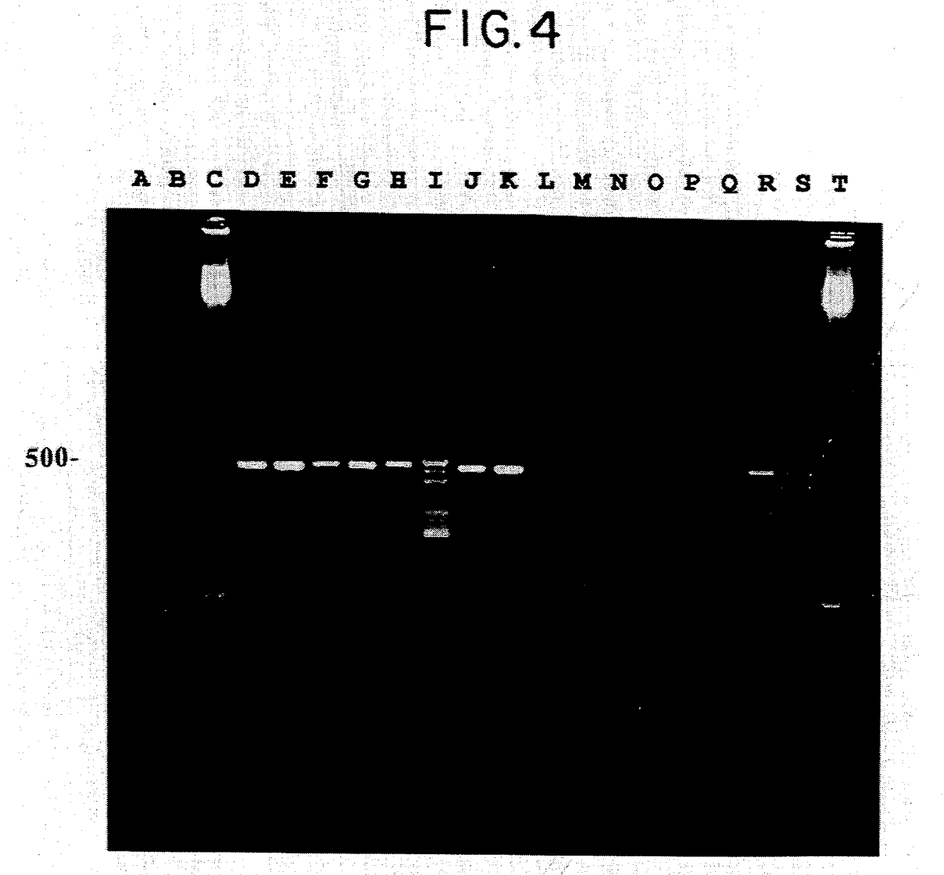
FIG. 4 is an ethidium bromide stained electrophoretic gel obtained from the analysis of various samples.

FIG. 4 is a photograph of the ethidium bromide stained electrophoretic gel obtained from the analysis of the various samples.

Lanes A and B contain aliquots of control PCR reactions 1 and 2 in which all the components of the reactions, as described in Example 15, were added except the polymerase. As expected, no amplification is seen. Lanes C and T contain a commercially available DNA size marker (123 bp DNA marker, Gibco BRL, Bethesda, Md.) and Lane I contains another commercially available DNA size marker (DNA Marker V, Boehringer Mannheim, Indianapolis, Ind.).

Lanes D-H contain the PCR products from reactions 3-7 of Table 4, respectively. In each case a well defined band corresponding to the 500 base pair DNA fragment is present demonstrating that efficient amplification was achieved with the various combinations of buffers and unmodified or biotinylated primers.

Analysis of material in the "support eluent" is shown in lanes J-N which correspond to reactions 3-7, respectively. The presence of the bands in lanes J and K demonstrates that amplification products from reactions that contain unmodified primers are not retained by the streptavidin agarose. The absence or marked decrease of the fragment in lanes L-N (from reactions 5-7) shows that DNA derived from the biotinylated trityl primers is bound by the support.

Recovery of bound biotinylated fragments was achieved by acid treatment of support bound DNA as shown in lanes O-S (from reactions 3-7). Lanes O and P correspond to the acid eluent derived from reactions 3 and 4, respectively. No DNA is present because these reactions contained unmodified primers and thus no DNA was bound to the streptavidin agarose. Lanes Q-S contain the acid eluent from reactions 5-7, respectively. The presence of the 500 base pair fragment in lanes Q-S demonstrates that 5'-modified support bound DNA can be recovered upon exposure of the support to conditions known to cleave the modified trityl group.

Equivalents

Those skilled in the art will recognize or be able to ascertain, using no more than routine experimentation, many equivalents to the specific embodiments of the invention described herein. These and all other equivalents are intended to be encompassed by the following claims.

We claim:

1. A compound represented by the formula:

2. A method of synthesizing a compound represented by the formula:

wherein X is $Cl$, $Br$, $I$ or $BF_4$, said method comprising the steps of:
  a) reacting 2-(4-bromophenyl)-4,4-dimethyl-1,3-oxazoline with magnesium to produce a Grignard reagent which is reacted with 4,4'-dimethoxy-benzophenone to produce 2-[4-((bis-4-methoxyphenyl)-hydroxymethyl)-phenyl]-4,4-dimethyloxazoline;
  b) sequentially reacting the product of step (a) with aqueous acid, base and acid to produce 4-carboxy-4',4''-dimethoxytriphenylmethanol;
  c) reacting the product of step (b) with N-hydroxysuccinimide to produce N-succinimidyl-4-[(bis-4-methoxyphyenyl)-hydroxymethyl]-benzoate; and
  d) reacting the product of step (c) with a reagent to replace the hydroxyl group with the leaving group X.

* * * * *